US009638578B2

(12) United States Patent
Tomioka

(10) Patent No.: US 9,638,578 B2
(45) Date of Patent: May 2, 2017

(54) TERAHERTZ WAVE DETECTING DEVICE, CAMERA, IMAGING APPARATUS, AND MEASURING APPARATUS

(71) Applicant: SEIKO EPSON CORPORATION, Tokyo (JP)

(72) Inventor: Hiroto Tomioka, Chino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 0 days.

(21) Appl. No.: 14/863,371

(22) Filed: Sep. 23, 2015

(65) Prior Publication Data

US 2016/0084702 A1   Mar. 24, 2016

(30) Foreign Application Priority Data

Sep. 24, 2014   (JP) ................. 2014-194032

(51) Int. Cl.
| | |
|---|---|
| *G01N 21/3581* | (2014.01) |
| *G01J 3/42* | (2006.01) |
| *G01J 5/34* | (2006.01) |
| *G01J 5/08* | (2006.01) |

(52) U.S. Cl.
CPC .............. *G01J 3/42* (2013.01); *G01J 5/0853* (2013.01); *G01J 5/34* (2013.01); *G01N 21/3581* (2013.01)

(58) Field of Classification Search
CPC .................. G01J 5/0853; G01J 5/34
See application file for complete search history.

(56) References Cited

U.S. PATENT DOCUMENTS

| | | | |
|---|---|---|---|
| 2005/0087689 A1* | 4/2005 | Tomozawa | H01L 37/025 |
| | | | 250/338.3 |
| 2009/0101297 A1* | 4/2009 | Jez | G01N 21/23 |
| | | | 162/198 |
| 2014/0264029 A1 | 9/2014 | Tomioka | |
| 2014/0361169 A1 | 12/2014 | Tomioka | |
| 2014/0361170 A1 | 12/2014 | Tomioka | |
| 2014/0361178 A1 | 12/2014 | Tomioka | |
| 2015/0035110 A1* | 2/2015 | Pisano | G01J 5/0853 |
| | | | 257/443 |

FOREIGN PATENT DOCUMENTS

| | | |
|---|---|---|
| JP | 2009-141661 A | 6/2006 |
| JP | 2013-044703 A | 3/2013 |
| JP | 2014-163674 A | 9/2014 |
| JP | 2014-235144 A | 12/2014 |
| JP | 2014-235145 A | 12/2014 |
| JP | 2014-235146 A | 12/2014 |

* cited by examiner

*Primary Examiner* — Yara B Green
(74) *Attorney, Agent, or Firm* — Maschoff Brennan

(57) ABSTRACT

A terahertz wave detecting device includes: a substrate; a first metal layer that is disposed above the substrate; a pyroelectric layer that is disposed on the first metal layer; and a second metal layer that is disposed on the pyroelectric layer, wherein the second metal layer has a periodic structure in which a unit structure is disposed in a predetermined period, and the pyroelectric layer absorbs terahertz waves being incident on the pyroelectric layer and converts the terahertz waves into heat and converts the converted heat into an electrical signal.

18 Claims, 10 Drawing Sheets

TERAHERTZ WAVE DETECTING DEVICE, CAMERA, IMAGING APPARATUS, AND MEASURING APPARATUS

BACKGROUND

1. Technical Field

The present invention relates to a terahertz wave detecting device, a camera, an imaging apparatus, and a measuring apparatus.

2. Related Art

Recently, there has been attention to terahertz waves that are electromagnetic waves having a frequency of greater than or equal to 100 GHz and less than or equal to 30 THz. Terahertz waves can be used in, for example, imaging, various types of measurement such as spectroscopic measurement, and non-destructive testing.

As such a detecting device (sensor) that detects terahertz waves, in JP-A-2013-44703, there is disclosed a structure in which a photothermal converter having a periodic structure formed therein and a pyroelectric body are thermally bonded. In such a detecting device, light is converted into heat by the photothermal converter. The heat changes electrical properties of the pyroelectric body, and the amount of light is detected.

In the detecting device disclosed in JP-A-2013-44703, however, thermal capacity is increased due to the photothermal converter disposed therein, and thus the speed of reaction of the detecting device may be decreased.

SUMMARY

An advantage of some aspects of the invention is to provide a terahertz wave detecting device capable of having a high speed of reaction by decreasing a thermal capacity. Another advantage of some aspects of the invention is to provide a camera, an imaging apparatus, and a measuring apparatus that include the terahertz wave detecting device.

A terahertz wave detecting device according to an aspect of the invention includes: a substrate; a first metal layer that is disposed above the substrate; a pyroelectric layer that is disposed on the first metal layer; and a second metal layer that is disposed on the pyroelectric layer, in which the second metal layer has a periodic structure in which a unit structure is disposed in a predetermined period, and the pyroelectric layer absorbs terahertz waves being incident on the pyroelectric layer and converts the terahertz waves into heat and converts the converted heat into an electrical signal.

In such a terahertz wave detecting device, a speed of reaction (speed of response) cab be increased by decreasing a thermal capacity in comparison with a case where a part that absorbs terahertz waves and converts the terahertz waves into heat and a part that converts the converted heat into an electrical signal are separately disposed.

In the disclosure of the invention, when the word "above" is used in a sentence such as "A certain one (hereinafter, referred to as "B") is formed "above" another certain one (hereinafter, referred to as "A").", the use of the word "above" is intended to include a case where B is directly formed on A and a case where B is formed on A through other objects.

In the terahertz wave detecting device according to the aspect of the invention, the predetermined period may be shorter than the wavelength of the terahertz waves in a vacuum that are absorbed into the pyroelectric layer.

In such a terahertz wave detecting device, terahertz waves used in irradiation can enter the pyroelectric layer and be multiply reflected between the unit structure and the first metal layer.

In the terahertz wave detecting device according to the aspect of the invention, the first metal layer and the second metal layer may be electrically connected to the pyroelectric layer.

In such a terahertz wave detecting device, a change in the amount of electric polarization of the pyroelectric layer can flow as a pyroelectric current in the metal layers in response to a temperature change in the pyroelectric layer.

The terahertz wave detecting device according to the aspect of the invention may further include: a supportive substrate that supports the first metal layer; and a supportive portion that supports the supportive substrate separately from the substrate.

In such a terahertz wave detecting device, the pyroelectric layer can be thermally separated from the substrate. Therefore, a temperature change in the pyroelectric layer due to terahertz wave irradiation can be accurately detected in such a terahertz wave detecting device.

In the terahertz wave detecting device according to the aspect of the invention, the thickness of the pyroelectric layer may be greater than or equal to 300 nm and less than or equal to 700 nm.

In such a terahertz wave detecting device, terahertz waves are more securely absorbed into the pyroelectric layer, and the speed of reaction of the terahertz wave detecting device can be increased.

In the terahertz wave detecting device according to the aspect of the invention, the first metal layer, the pyroelectric layer, and the second metal layer may constitute a unit cell, and the unit cell may be disposed in plural numbers.

In such a terahertz wave detecting device, for example, by decreasing the distance between adjacent unit cells, the overall efficiency of the terahertz wave detecting device in absorbing terahertz waves can be increased in comparison with a case where only one unit cell is disposed. Accordingly, sensitivity of the terahertz wave detecting device can be improved.

In the terahertz wave detecting device according to the aspect of the invention, the unit structure may include a region on the pyroelectric layer where the second metal layer is disposed, and a region on the pyroelectric layer where the second metal layer is not disposed, and the unit cell may be disposed in plural numbers having different widths of the region where the second metal layer is not disposed.

In such a terahertz wave detecting device, terahertz waves of different frequencies (different wavelengths) can be detected.

The terahertz wave detecting device according to the aspect of the invention may further include: a reflective layer that reflects the terahertz waves below the first metal layer.

In such a terahertz wave detecting device, terahertz waves that are directed toward the substrate without being absorbed into the pyroelectric layer can be reflected by the reflective layer toward the pyroelectric layer. Accordingly, the efficiency in absorbing terahertz waves into the pyroelectric layer can be increased, and sensitivity of the terahertz wave detecting device can be improved.

In the disclosure of the invention, when the word "below" is used in a sentence such as "A certain one (hereinafter, referred to as "D") is formed "below" another certain one (hereinafter, referred to as "C").", the use of the word "below" is intended to include a case where D is directly formed under C and a case where D is formed under C through other objects.

A camera according to another aspect of the invention includes: a terahertz wave generating unit that generates terahertz waves; a terahertz wave detecting unit that includes the terahertz wave detecting device according to the aspect of the invention which detects the terahertz waves emitted from the terahertz wave generating unit and transmitted through or reflected by an object; and a storage unit that stores a detection result of the terahertz wave detecting unit.

Since such a camera includes the terahertz wave detecting device according to the aspect of the invention, the speed of reaction of the camera can be increased.

An imaging apparatus according to still another aspect of the invention includes: a terahertz wave generating unit that generates terahertz waves; a terahertz wave detecting unit that includes the terahertz wave detecting device according to the aspect of the invention which detects the terahertz waves emitted from the terahertz wave generating unit and transmitted through or reflected by an object; and an image forming unit that generates an image of the object on the basis of a detection result of the terahertz wave detecting unit.

Since such an imaging apparatus includes the terahertz wave detecting device according to the aspect of the invention, the speed of reaction of the imaging apparatus can be increased.

A measuring apparatus according to yet another aspect of the invention includes: a terahertz wave generating unit that generates terahertz waves; a terahertz wave detecting unit that includes the terahertz wave detecting device according to the aspect of the invention which detects the terahertz waves emitted from the terahertz wave generating unit and transmitted through or reflected by an object; and a measuring unit that measures the object on the basis of a detection result of the terahertz wave detecting unit.

Since such a measuring apparatus includes the terahertz wave detecting device according to the aspect of the invention, the speed of reaction of the measuring apparatus can be increased.

BRIEF DESCRIPTION OF THE DRAWINGS

The invention will be described with reference to the accompanying drawings, wherein like numbers reference like elements.

DESCRIPTION OF EXEMPLARY EMBODIMENTS

Hereinafter, an exemplary embodiment of the invention will be described in detail by using the drawings. The embodiment described below does not unduly limit the content of the invention disclosed in the appended claims. In addition, all configurations described below are not necessarily constituent elements of the invention.

1. Terahertz Wave Detecting Device

Figure 1:
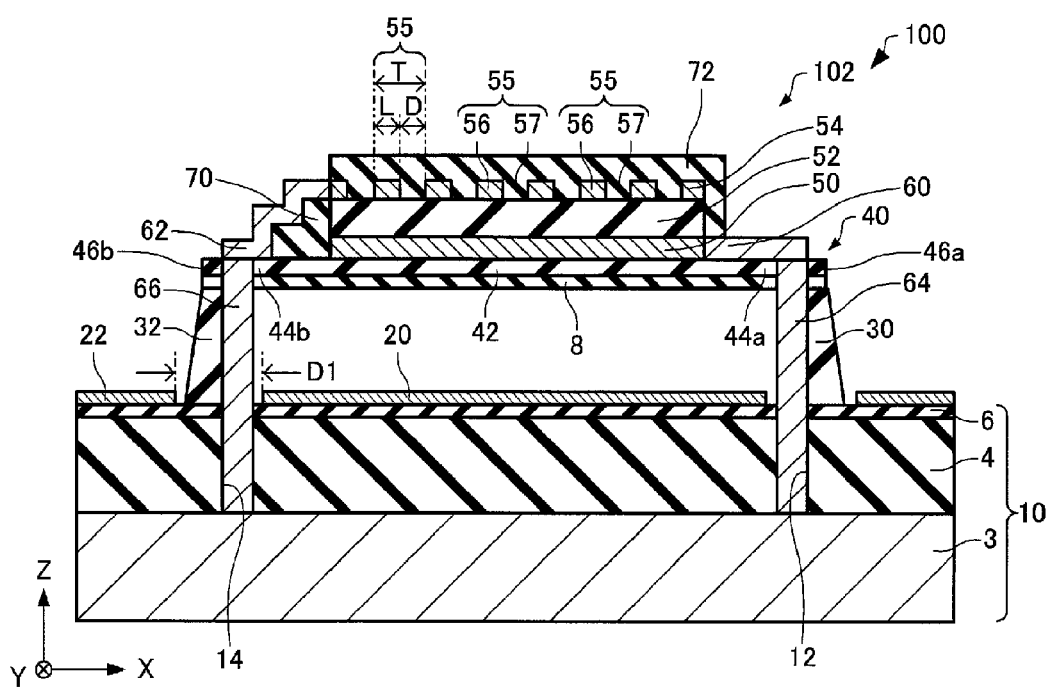
FIG. 1 is a sectional view schematically illustrating a terahertz wave detecting device according to an embodiment.
Figure 2:
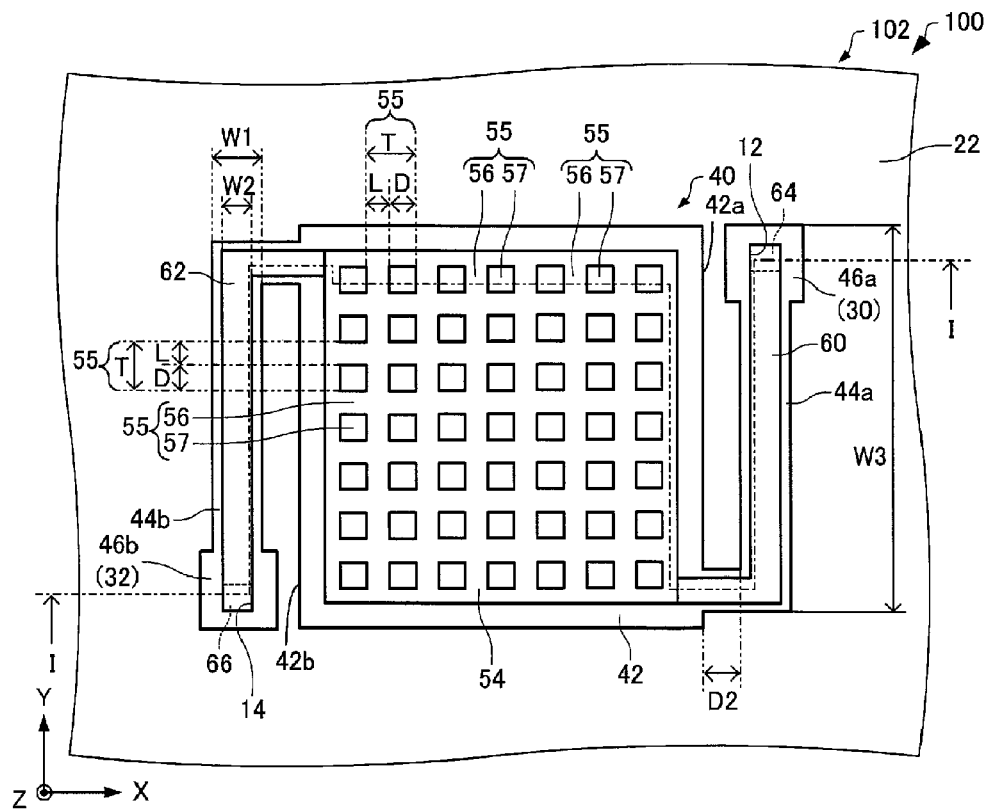
FIG. 2 is a plan view schematically illustrating the terahertz wave detecting device according to the embodiment.
Figure 3:
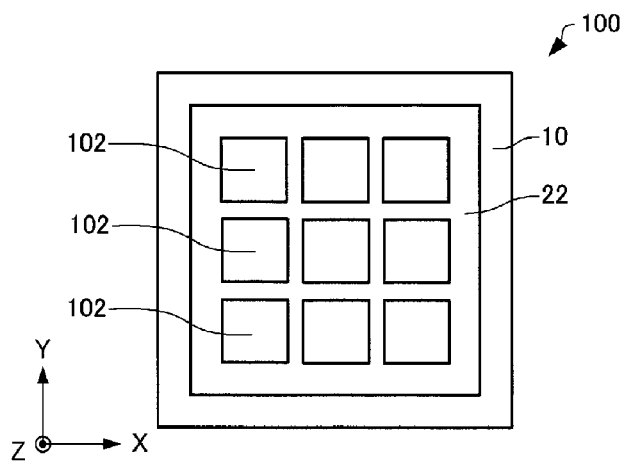
FIG. 3 is a plan view schematically illustrating the terahertz wave detecting device according to the embodiment.

First, a terahertz wave detecting device according to the present embodiment will be described with reference to the drawings. FIG. 1 is a sectional view schematically illustrating a unit cell 102 of a terahertz wave detecting device 100 according to the present embodiment. FIG. 2 is a plan view schematically illustrating the unit cell 102 of the terahertz wave detecting device 100 according to the present embodiment. FIG. 3 is a plan view schematically illustrating the terahertz wave detecting device 100 according to the present embodiment. FIG. 1 is a sectional view taken along line I-I of FIG. 2. In FIG. 1 to FIG. 3, three axes orthogonal with respect to each other are illustrated as an X axis, a Y axis, and a Z axis.

The terahertz wave detecting device 100, as illustrated in FIG. 1 to FIG. 3, includes a substrate 10, a reflective layer 20, supportive portions 30 and 32, a supportive substrate (membrane) 40, a first metal layer 50, a pyroelectric layer 52, a second metal layer 54, interconnect layers 60 and 62, contact portions 64 and 66, and insulating layers 70 and 72. The supportive portions 30 and 32, the supportive substrate 40, the metal layers 50 and 54, the pyroelectric layer 52, the interconnect layers 60 and 62, the contact portions 64 and 66, and the insulating layers 70 and 72 constitute the unit cell 102. In FIG. 2, the insulating layers 70 and 72 are not illustrated for convenience of description. In addition, in FIG. 3, the unit cell 102 is illustrated in a simplified manner for convenience of description.

The shape of the substrate 10 is, for example, a plate. The substrate 10 includes a supportive substrate 3, an interlayer insulating layer 4, and a first protective layer 6. The thickness of the supportive substrate 3 is, for example, greater than or equal to 10 µm and less than or equal to 500 µm. The material of the supportive substrate 3 is, for example, silicon. The interlayer insulating layer 4 is disposed on the supportive substrate 3. The thickness of the interlayer insulating layer 4 is, for example, greater than or equal to 10 nm and less than or equal to 10 µm. The material of the interlayer insulating layer 4 is, for example, silicon oxide. The first protective layer 6 is disposed on the interlayer insulating layer 4. The thickness of the first protective layer 6 is, for example, greater than or equal to 10 nm and less than or equal to 10 µm. The material of the first protective layer 6 is, for example, aluminum oxide (alumina). The first protective layer 6 can protect the interlayer insulating layer 4 at the time of etching a below-described sacrificial layer 80.

The reflective layer 20 is disposed below the first metal layer 50. In the example illustrated, the reflective layer 20 is disposed on the substrate 10. The thickness (Z-axis directional size) of the reflective layer 20 is, for example, greater than or equal to 10 nm and less than or equal to 1 µm. The material of the reflective layer 20 is, for example, gold, silver, platinum, copper, aluminum, or titanium. The reflective layer 20 can reflect, toward the pyroelectric layer 52, terahertz waves that are directed toward the substrate 10 without being absorbed into the pyroelectric layer 52.

The reflective layer 20, provided that the reflective layer 20 is disposed below the first metal layer 50, may be disposed between the supportive substrate 3 and the interlayer insulating layer 4 or may be disposed between the interlayer insulating layer 4 and the first protective layer 6.

In the example illustrated, a layer 22 is disposed in a region of the substrate 10 that does not overlap with the unit cell 102 in a plan view (when viewed from the Z-axis direction). The layer 22 has the same material as the reflective layer 20. A distance D1 (refer to FIG. 1) between the reflective layer 20 and the layer 22 is, for example, greater than or equal to 1 µm and less than or equal to 50 µm.

The unit cell 102 is disposed on the substrate 10. The unit cell 102 is disposed in plural numbers. Although nine unit cells 102 are disposed in the example illustrated in FIG. 3, the number thereof is not particularly limited. The unit cells 102 are arranged into, for example, a matrix. The distance between adjacent unit cells 102 is, for example, greater than or equal to 1 µm and less than or equal to 50 µm. The wavelengths of terahertz waves to be detected are, for example, the same in the plurality of unit cells 102.

The supportive portions 30 and 32 are disposed on the substrate 10. The supportive portions 30 and 32 are separated from each other. The material of the supportive portions 30 and 32 is, for example, silicon oxide. The supportive portions 30 and 32 support the supportive substrate 40 separately from the substrate 10.

The supportive substrate 40 is supported by the supportive portions 30 and 32 above the substrate 10 separately from the substrate 10. In the example illustrated, the supportive substrate 40 is disposed separately from the reflective layer 20. The distance between the supportive substrate 40 and the reflective layer 20 is, for example, greater than or equal to 100 nm and less than or equal to 10 µm.

The supportive substrate 40 has, for example, a three-layer structure of a silicon dioxide layer, a silicon nitride layer, and a silicon dioxide layer. In the example illustrated, a second protective layer 8 is disposed under the supportive substrate 40. The thickness of the second protective layer 8 is, for example, greater than or equal to 10 nm and less than or equal to 10 µm. The material of the second protective layer 8 is, for example, aluminum oxide. The second protective layer 8 can protect the supportive substrate 40 at the time of etching the below-described sacrificial layer 80. The supportive substrate 40 includes a base portion 42, arm portions 44a and 44b, and fixed portions 46a and 46b.

The shape of the base potion 42 is, for example, a plate. In the example illustrated in FIG. 2, the planar shape (shape viewed from the Z-axis direction) of the base portion 42 is a square. The X-axis directional size of the base portion 42 is, for example, greater than or equal to 5 µm and less than or equal to 500 µm. The Y-axis directional size of the base portion 42 is, for example, the same as the X-axis directional size of the base portion 42. The thickness of the base portion 42 is, for example, greater than or equal to 10 nm and less than or equal to 1 µm. The base portion 42 supports the first metal layer 50.

The first arm potion 44a connects the base portion 42 and the first fixed portion 46a. The second arm portion 44b connects the base portion 42 and the second fixed portion 46b. The arm portions 44a and 44b, as illustrated in FIG. 2, extend in opposite directions from facing faces (side faces) 42a and 42b of the base portion 42, bend at a right angle, and reach the fixed portions 46a and 46b. A width W1 (refer to FIG. 2) of the arm portions 44a and 44b is, for example, greater than or equal to 500 nm and less than or equal to 10 µm. A distance D2 (refer to FIG. 2) between the first arm portion 44a and the base portion 42 is, for example, greater than or equal to 500 nm and less than or equal to 10 µm. The distance between the second arm portion 44b and the base portion 42 is, for example, the same as D2.

The fixed portions 46a and 46b are disposed on the supportive portions 30 and 32. Specifically, the first fixed portion 46a is fixed onto the first supportive portion 30, and the second fixed portion 46b is fixed onto the second supportive portion 32. In the example illustrated in FIG. 2, the planar shapes of the fixed portions 46a and 46b are squares. A sum W3 (refer to FIG. 2) of the Y-axis directional size of the first arm portion 44a and the Y-axis directional size of the first fixed portion 46a is, for example, greater than or equal to 5 µm and less than or equal to 500 µm. The sum of the Y-axis directional size of the second arm portion 44b and the Y-axis directional size of the second fixed portion 46b is, for example, the same as W3.

The first metal layer 50 is disposed above the substrate 10. In the example illustrated, the first metal layer 50 is disposed on the base portion 42 of the supportive substrate 40. The thickness of the first metal layer 50 is, for example, greater than or equal to 1 nm and less than or equal to 500 nm. The first metal layer 50 has, for example, a three-layer structure in which an iridium layer, an iridium oxide layer, and a platinum layer are stacked in order from the base portion 42 side. The first metal layer 50 is electrically connected to the pyroelectric layer 52. The first metal layer 50 is one of electrodes used in detecting a pyroelectric current of the pyroelectric layer 52.

The pyroelectric layer 52 is disposed on the first metal layer 50. The thickness of the pyroelectric layer 52 is, for example, greater than or equal to 300 nm and less than or equal to 700 nm. The material of the pyroelectric layer is a dielectric that can exhibit pyroelectric effect. Specifically, the material of the pyroelectric layer 52 is lead zirconate titanate (PZT). The pyroelectric layer 52 can absorb and convert terahertz waves being incident on the pyroelectric layer 52 into heat and can convert the converted heat into an electrical signal.

The second metal layer 54 is disposed on the pyroelectric layer 52. The planar shape of the second metal layer 54 is, for example, a square. The X-axis directional size of the second metal layer 54 is, for example, greater than or equal to 5 μm and less than or equal to 500 μm. The Y-axis directional size of the second metal layer 54 is, for example, the same as the X-axis directional size of the second metal layer 54. When the X-axis directional size and the Y-axis directional size of the second metal layer 54 are less than 10 nm, the efficiency in absorbing terahertz waves into the pyroelectric layer 52 may decrease. When the X-axis directional size and the Y-axis directional size of the second metal layer 54 are greater than 200 μm, the supportive portions 30 and 32 may not support the supportive substrate 40 separately from the substrate 10. The thickness of the second metal layer 54 is, for example, greater than or equal to 1 nm and less than or equal to 500 nm.

The second metal layer 54 has, for example, a three-layer structure in which a platinum layer, an iridium oxide layer, and an iridium layer are stacked in order from the pyroelectric layer 52 side. The second metal layer 54 is electrically connected to the pyroelectric layer 52. The second metal layer 54 is the other of the electrodes used in detecting a pyroelectric current of the pyroelectric layer 52. The reflectivity of the metal layers 50 and 54 with respect to terahertz waves is, for example, greater than or equal to 90%.

The material of the metal layers 50 and 54 is not limited to the above example and may be, for example, metal such as gold, copper, iron, aluminum, zinc, chromium, lead, and titanium or an alloy such as Nichrome.

The second metal layer 54 has a periodic structure in which a unit structure 55 is disposed in a predetermined period. The unit structure 55 is a part of a metamaterial. A metamaterial is an artificial material in which a unit structure that is sufficiently small in comparison with the wavelength of electromagnetic waves (terahertz waves) is periodically arranged. The metamaterial is configured to behave as a homogeneous medium with respect to the electromagnetic waves. Physical property values (dielectric constant and magnetic permeability) of the metamaterial can be freely adjusted by the structure and arrangement of the unit structures.

The unit structure 55 includes a first region 56 and a second region 57. The first region 56 is where the second metal layer 54 is disposed on the pyroelectric layer 52, and the second region 57 is where the second metal layer 54 is not disposed on the pyroelectric layer 52. In the example illustrated, the planar shape of the first region 56 and the planar shape of the second region 57 are squares. The second region 57 is a region that is formed by an opening portion disposed in the second metal layer 54 (opening portion that passes through the second metal layer 54).

The unit structure 55, for example, is periodically disposed with a length of a period T in the X-axis direction. In other words, the first region 56 having a size (width) L and the second region 57 having a size (width) D are alternately arranged in the X-axis direction, and the sum of L and D is T (L+D=T). The unit structure 55, for example, is periodically disposed with a length of the period T in the Y-axis direction. In other words, the first region 56 having the width L and the second region 57 having the width D are alternately arranged in the Y-axis direction, and the sum of L and D is T (L+D=T).

The period T of the unit structure 55 is shorter than the wavelength of terahertz waves in a vacuum that are absorbed into the pyroelectric layer 52. That is, the width L of the first region 56 and the width D of the second region 57 of the unit structure 55 are shorter than the wavelength of terahertz waves in a vacuum that are absorbed into the pyroelectric layer 52. The width L of the first region 56 is, for example, greater than or equal to 0.1 μm and less than or equal to 3 μm. The wavelength (frequency) of terahertz waves absorbed into the pyroelectric layer 52 is determined by the value of the width L. The width D of the second region 57 is, for example, greater than or equal to 0.1 μm and less than or equal to 3 μm. The absorbance of the pyroelectric layer 52 for terahertz waves is determined by the width D.

The first interconnect layer 60 is disposed on the first arm portion 44a. The first interconnect layer 60 is connected to the first metal layer 50 and to the first contact portion 64. The second interconnect layer 62 is disposed on the second arm portion 44b. The second interconnect layer 62 is connected to the second metal layer 54 and to the second contact portion 66. A width W2 (refer to FIG. 2) of the interconnect layers 60 and 62 is, for example, greater than or equal to 500 nm and less than or equal to 10 μm. The thicknesses of the interconnect layers 60 and 62 are, for example, greater than or equal to 10 nm and less than or equal to 100 nm. The material of the interconnect layers 60 and 62 is not particularly limited, provided that the material has conductivity. The interconnect layers 60 and 62 may be formed with wire bonding.

The first contact portion 64 is disposed in a first contact hole 12 that is formed in the first fixed portion 46a, the second protective layer 8, the first supportive portion 30, the first protective layer 6, and the interlayer insulating layer 4. The second contact portion 66 is disposed in a second contact hole 14 that is formed in the second fixed portion 46b, the second protective layer 8, the second supportive portion 32, the first protective layer 6, and the interlayer insulating layer 4. The thicknesses of the contact portions 64 and 66 are, for example, greater than or equal to 100 nm and less than or equal to 10 μm. The material of the contact portions 64 and 66 is not particularly limited, provided that the material has conductivity.

The contact portions 64 and 66 are electrically connected to, for example, an unillustrated circuit portion that is disposed on the supportive substrate 3. The contact portions 64 and 66 can electrically connect the metal layers 50 and 54 to the circuit portion.

The insulating layers 70 and 72 are disposed to cover the pyroelectric layer 52. In the example illustrated, the first insulating layer 70 is disposed on a side of the pyroelectric layer 52 and on a side of the first metal layer 50. The second insulating layer 72 is disposed on a side of the pyroelectric layer 52, on a side of the second metal layer 54, on the pyroelectric layer 52, and on the second metal layer 54. The thickness of the second insulating layer 72 (thickness of the second insulating layer 72 on the second metal layer 54) is, for example, greater than or equal to 1 nm and less than or equal to 100 nm. The material of the insulating layers 70 and 72 is, for example, aluminum oxide or silicon oxide. The insulating layers 70 and 72 can suppress foreign objects attaching to the pyroelectric layer 52 and to the metal layers 50 and 54. Furthermore, the insulating layers 70 and 72 can suppress oxidation of the pyroelectric layer 52 and the metal layers 50 and 54.

Next, an operation of the terahertz wave detecting device 100 will be described.

When the unit cell 102 of the terahertz wave detecting device 100 is irradiated with terahertz waves, the terahertz waves, since the period T of the unit structure 55 of the second metal layer 54 is shorter than the wavelength of the terahertz waves, enters the pyroelectric layer 52 and are multiply reflected between the unit structure 55 and the first metal layer 50. Specifically, terahertz waves are multiply reflected between a face of the unit structure 55 that is in contact with the pyroelectric layer 52 and a face of the first metal layer 50 that is in contact with the pyroelectric layer 52, and this causes resonance and generates standing waves. The frequency of resonating terahertz waves (resonance frequency) can be appropriately changed by the shape and size of the unit structure 55. As such, terahertz waves can be confined to the pyroelectric layer 52 in the terahertz wave detecting device 100.

Multiple reflection of terahertz waves, which are confined to the pyroelectric layer 52, between the unit structure 55 that interposes the pyroelectric layer 52 and the first metal layer 50 causes a dielectric loss in the pyroelectric layer 52, and this generates heat. As such, the pyroelectric layer 52 can absorb and convert terahertz waves into heat. In addition, atoms and electrons constituting the face of the unit structure 55 that is in contact with the pyroelectric layer 52 and atoms and electrons constituting the face of the first metal layer 50 that is in contact with the pyroelectric layer 52 vibrate, and this generates heat.

A temperature change occurs in the pyroelectric layer 52 due to the generated heat. Then, a change in the amount of electric polarization of the pyroelectric layer 52 flows as a pyroelectric current in the metal layers 50 and 54 in response to the temperature change in the pyroelectric layer 52. As such, the pyroelectric layer 52 can convert a temperature change (heat) into an electrical signal.

The current (electrical signal) that flows in the metal layers 50 and 54 in response to the pyroelectric effect of the pyroelectric layer 52 reaches the circuit portion (not illustrated) disposed in the supportive substrate 3. In the circuit portion, terahertz waves are detected from the electrical signal. As described herebefore, the terahertz wave detecting device 100 can detect terahertz waves.

In the terahertz wave detecting device 100, electrical coupling occurs, in adjacent unit structures 55, between the standing wave which occurs between one of the unit structures 55 and the first metal layer 50 and the standing wave which occurs between the other of the unit structures 55 and the first metal layer 50. Accordingly, the absorbance of the pyroelectric layer 52 for terahertz waves can be improved.

In the terahertz wave detecting device 100, terahertz waves are multiply reflected not only between the unit structure 55 and the first metal layer 50 but also, for example, between adjacent unit structures 55, and this causes resonance.

The terahertz wave detecting device 100, for example, has the following features.

In the terahertz wave detecting device 100, the second metal layer 54 has a periodic structure in which the unit structure 55 is disposed in the predetermined period T, and the pyroelectric layer 52 absorbs terahertz waves being incident on the pyroelectric layer 52 and converts the terahertz waves into heat and converts the converted heat into an electrical signal. Thus, the terahertz wave detecting device 100 can have a high speed of reaction (speed of response) of the terahertz wave detecting device 100 by decreasing a thermal capacity in comparison with a case where a part that absorbs terahertz waves and converts the terahertz waves into heat and a part that converts the converted heat into an electrical signal are separately disposed.

In the case where, for example, a first part that absorbs terahertz waves and converts the terahertz waves into heat and a second part that converts the converted heat into an electrical signal are separately disposed, the heat of the first part is required to be transferred to the second part, and the heat transfer results in a time loss. Thus, the speed of reaction of the terahertz wave detecting device may be decreased.

The terahertz wave detecting device 100 can detect an electrical signal caused by terahertz waves without applying an external current or voltage. Thus, noise due to applying a current or voltage is not generated. Therefore, the terahertz wave detecting device 100 can suppress a decrease in detection sensitivity due to electrical noise.

In the terahertz wave detecting device 100, the predetermined period T of the unit structure 55 is shorter than the wavelength of terahertz waves in a vacuum that are absorbed into the pyroelectric layer 52. Thus, terahertz waves with which the unit cell 102 of the terahertz wave detecting device 100 is irradiated can enter the pyroelectric layer 52 and be multiply reflected between the unit structure 55 and the first metal layer 50.

In the terahertz wave detecting device 100, the first metal layer 50 and the second metal layer 54 are electrically connected to the pyroelectric layer 52. Thus, in the terahertz wave detecting device 100, a change in the amount of electric polarization of the pyroelectric layer 52 flows as a pyroelectric current in the metal layers 50 and 54 in response to a temperature change in the pyroelectric layer 52.

The terahertz wave detecting device 100 includes the supportive substrate 40, which supports the first metal layer 50, and the supportive portions 30 and 32, which support the supportive substrate 40 separately from the substrate 10. Thus, in the terahertz wave detecting device 100, the pyroelectric layer 52 can be thermally separated from the substrate 10. Therefore, in the terahertz wave detecting device 100, heat transfer can be suppressed between the plurality of unit cells 102. Furthermore, in the terahertz wave detecting device 100, a temperature change in the pyroelectric layer due to terahertz wave irradiation can be accurately detected.

In the terahertz wave detecting device 100, the thickness of the pyroelectric layer 52 is, for example, greater than or equal to 300 nm and less than or equal to 700 nm. Thus, in the terahertz wave detecting device 100, terahertz waves are more securely absorbed into the pyroelectric layer 52, and the speed of reaction of the terahertz wave detecting device 100 can be increased. When the thickness of the pyroelectric layer is less than 300 nm, terahertz waves may not be sufficiently absorbed into the pyroelectric layer. When the thickness of the pyroelectric layer is greater than 700 nm, it takes time for complete polarization in the pyroelectric layer, and the speed of reaction of the terahertz wave detecting device may be decreased. Furthermore, when the thickness of the pyroelectric layer is greater than 700 nm, cracks may be generated in the pyroelectric layer.

In the terahertz wave detecting device 100, the first metal layer 50, the pyroelectric layer 52, and the second metal layer 54 constitute the unit cell 102, and the unit cell 102 is disposed in plural numbers. Thus, for example, by decreasing the distance between adjacent unit cells 102 in the terahertz wave detecting device 100, the overall efficiency of the terahertz wave detecting device 100 in absorbing terahertz waves can be increased in comparison with a case where only one unit cell is disposed. Accordingly, sensitivity of the terahertz wave detecting device 100 can be improved.

The terahertz wave detecting device 100 includes the reflective layer 20, which reflects terahertz waves, below the first metal layer 50. Thus, in the terahertz wave detecting device 100, terahertz waves that are directed toward the substrate 10 without being absorbed into the pyroelectric layer 52 can be reflected by the reflective layer 20 toward the pyroelectric layer 52. Accordingly, the efficiency in absorbing terahertz waves into the pyroelectric layer 52 can be increased, and sensitivity of the terahertz wave detecting device 100 can be improved.

2. Method for Manufacturing Terahertz Wave Detecting Device

Next, a method for manufacturing the terahertz wave detecting device according to the present embodiment will be described with reference to the drawings. FIG. 4 to FIG. 9 are sectional views schematically illustrating a process of manufacturing the terahertz wave detecting device 100 according to the present embodiment and are corresponding to FIG. 1.

Figure 4:
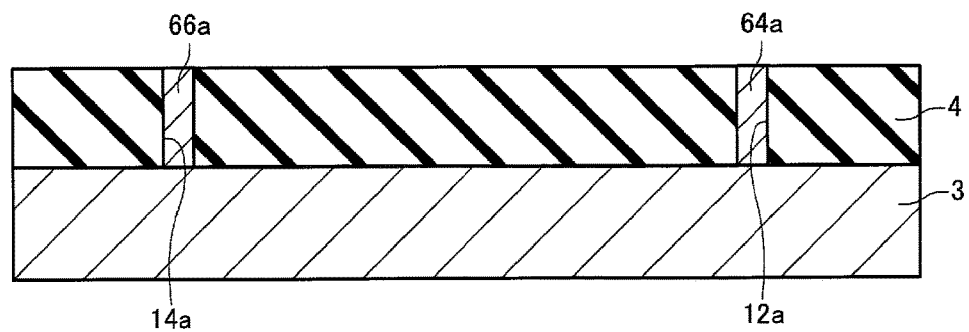
FIG. 4 is a sectional view schematically illustrating a process of manufacturing the terahertz wave detecting device according to the embodiment.

The interlayer insulating layer 4 is formed on the supportive substrate 3 as illustrated in FIG. 4. The interlayer insulating layer 4 is formed by, for example, chemical vapor deposition (CVD).

Next, contact holes 12a and 14a are formed by patterning (patterning through photolithography and etching) the interlayer insulating layer 4. Next, contact portions 64a and 66a are respectively formed in the contact holes 12a and 14a. The contact portions 64a and 66a are formed by, for example, plating or sputtering.

Figure 5:
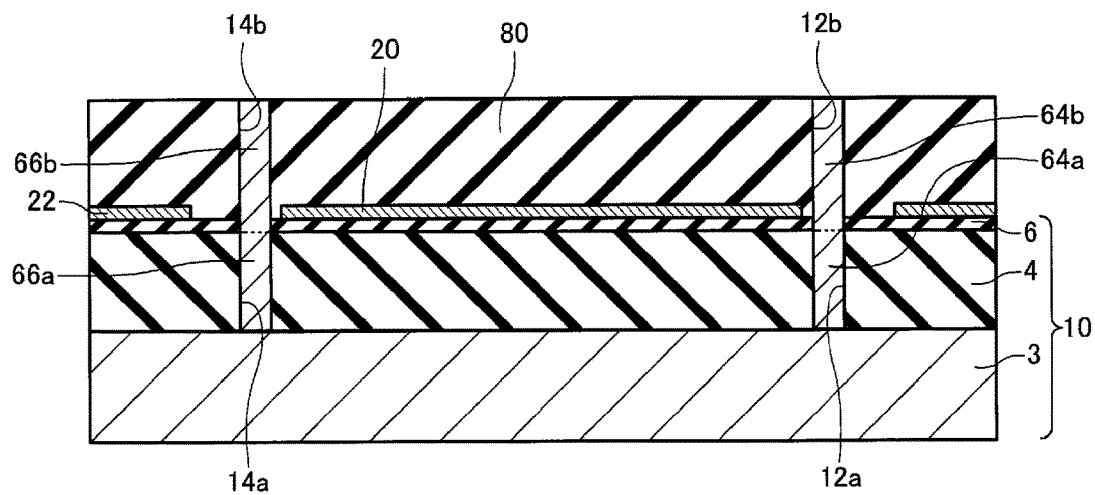
FIG. 5 is a sectional view schematically illustrating the process of manufacturing the terahertz wave detecting device according to the embodiment.

The first protective layer 6 is formed on the interlayer insulating layer 4 as illustrated in FIG. 5. The first protective layer 6 is formed by, for example, CVD or sputtering. Accordingly, the substrate 10 that includes the supportive substrate 3, the interlayer insulating layer 4, and the first protective layer 6 can be formed.

Next, the reflective layer 20 and the layer 22 are formed on the first protective layer 6. The reflective layer 20 and the layer 22 are formed by, for example, depositing a conductive layer (not illustrated) through sputtering, vacuum deposition, or the like and then patterning the conductive layer.

Next, the sacrificial layer 80 is formed on the first protective layer 6, on the reflective layer 20, and on the layer 22. The sacrificial layer 80 is formed by, for example, CVD. The material of the sacrificial layer 80 is, for example, silicon oxide.

Next, contact holes 12b and 14b are formed by patterning the sacrificial layer 80 and the first protective layer 6. The contact holes 12b and 14b are respectively formed such that the contact portions 64a and 66a are exposed. Next, contact portions 64b and 66b are respectively formed in the contact holes 12b and 14b. The contact portions 64b and 66b are formed to be respectively connected to the contact portions 64a and 66a. The contact portions 64b and 66b are formed by, for example, plating or sputtering.

Figure 6:
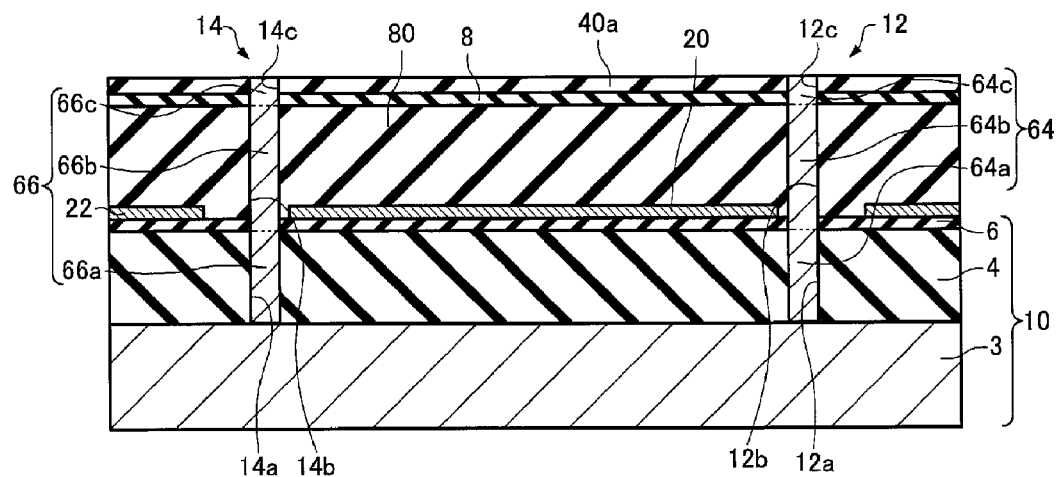
FIG. 6 is a sectional view schematically illustrating the process of manufacturing the terahertz wave detecting device according to the embodiment.

The second protective layer 8 is formed on the sacrificial layer 80 as illustrated in FIG. 6. The second protective layer 8 is formed by, for example, CVD or sputtering. Next, a layer 40a that becomes the supportive substrate 40 is formed on the second protective layer 8. The layer 40a is formed by, for example, CVD or sputtering.

Next, contact holes 12c and 14c are formed by patterning the second protective layer 8 and the layer 40a. The contact holes 12c and 14c are respectively formed such that the contact portions 64b and 66b are exposed. Next, contact portions 64c and 66c are respectively formed in the contact holes 12c and 14c. The contact portions 64c and 66c are formed to be respectively connected to the contact portions 64b and 66b. The contact portions 64c and 66c are formed by, for example, plating or sputtering.

By performing the process thus far, the first contact hole 12 configured of the contact holes 12a, 12b, and 12c and the second contact hole 14 configured of the contact holes 14a, 14b, and 14c can be formed. In addition, the first contact portion 64 configured of the contact portions 64a, 64b, and 64c and the second contact portion 66 configured of the contact portions 66a, 66b, and 66c can be formed.

Figure 7:
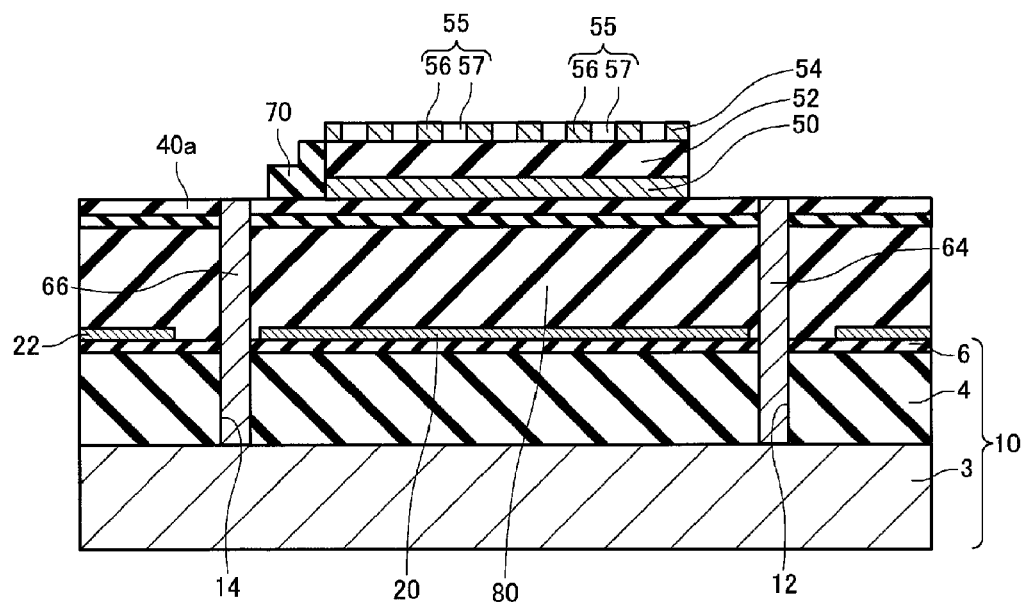
FIG. 7 is a sectional view schematically illustrating the process of manufacturing the terahertz wave detecting device according to the embodiment.

The first metal layer 50, the pyroelectric layer 52, and the second metal layer 54 are formed in this order on the layer 40a as illustrated in FIG. 7. The metal layers 50 and 54 are formed by, for example, deposition through sputtering and patterning. The second metal layer 54 is formed such that the unit structure 55 having the first region 56 and the second region 57 is disposed in plural numbers therein. The pyroelectric layer 52 is formed by, for example, deposition through sputtering or sol-gel and patterning.

Next, the first insulating layer 70 is formed on a side of the first metal layer 50 and on a side of the pyroelectric layer 52 on the layer 40a. The first insulating layer 70 is formed by, for example, deposition through sputtering or CVD and patterning.

Figure 8:
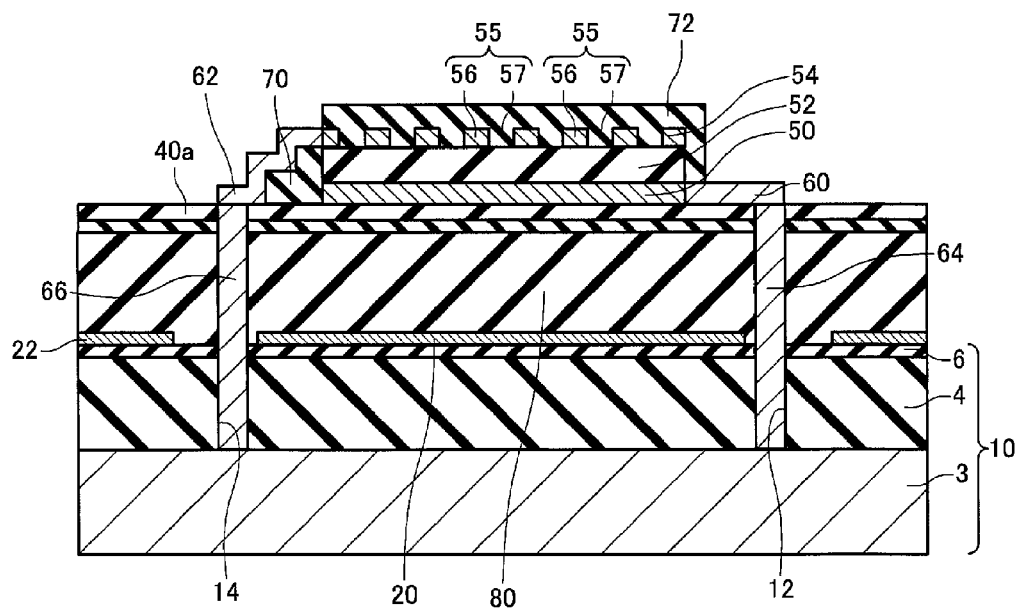
FIG. 8 is a sectional view schematically illustrating the process of manufacturing the terahertz wave detecting device according to the embodiment.

The first interconnect layer 60 is formed on the layer 40a to electrically connect the first metal layer 50 and the first contact portion 64 as illustrated in FIG. 8. Furthermore, the second interconnect layer 62 is formed on the layer 40a and on the first insulating layer 70 to electrically connect the second metal layer 54 and the second contact portion 66. The interconnect layers 60 and 62 are formed by, for example, plating or sputtering.

Next, the second insulating layer 72 is formed on the second metal layer 54 and on the pyroelectric layer 52. The second insulating layer 72 is formed by, for example, deposition through sputtering or CVD and patterning.

Figure 9:
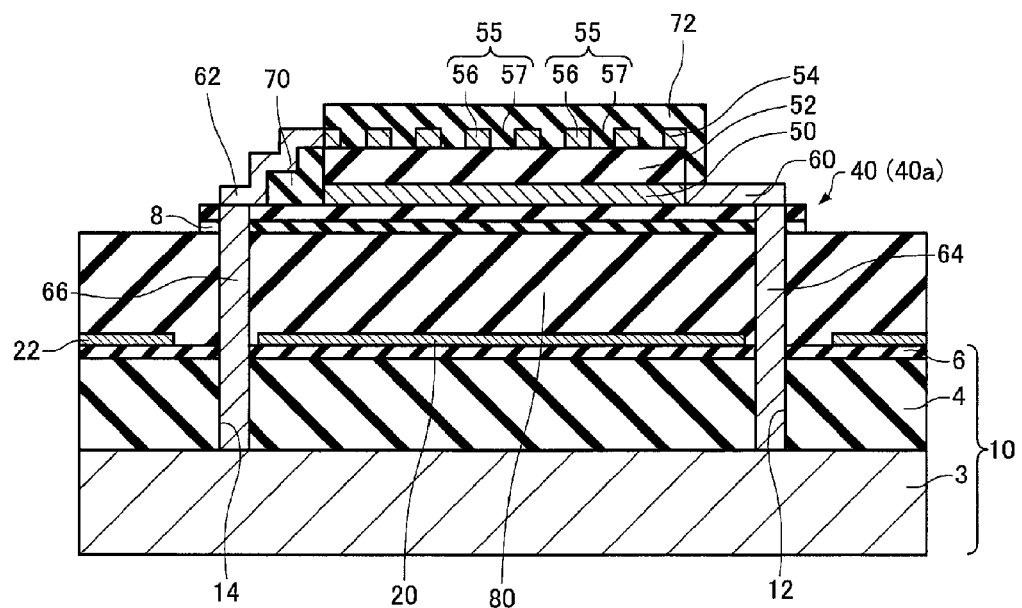
FIG. 9 is a sectional view schematically illustrating the process of manufacturing the terahertz wave detecting device according to the embodiment.

The layer 40a and the second protective layer 8 are patterned as illustrated in FIG. 9. Accordingly, the supportive substrate 40 that includes the base portion 42, the arm portions 44a and 44b, and the fixed portions 46a and 46b can be formed.

The sacrificial layer 80 is removed as illustrated in FIG. 1. The removal of the sacrificial layer 80 is performed by, for example, etching with the supportive substrate 40 as a mask. Accordingly, the supportive portions 30 and 32 can be formed.

By performing the process thus far, the terahertz wave detecting device 100 can be manufactured.

3. Modification Example of Terahertz Wave Detecting Device

Figure 10:
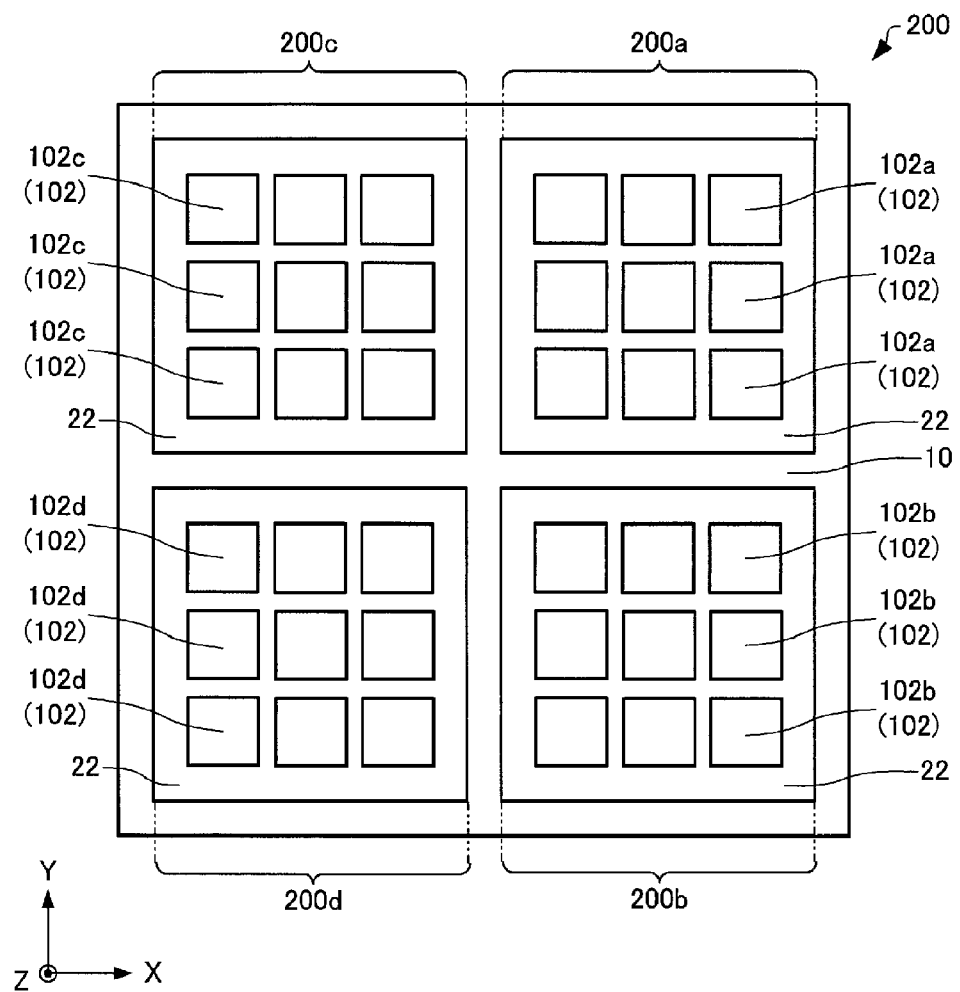
FIG. 10 is a plan view schematically illustrating a terahertz wave detecting device according to a modification example of the embodiment.

Next, a terahertz wave detecting device according to a modification example of the present embodiment will be described with reference to the drawings. FIG. 10 is a plan view schematically illustrating a terahertz wave detecting device 200 according to the modification example of the present embodiment. In FIG. 10, the unit cell 102 is illustrated in a simplified manner for convenience of description. In FIG. 10, three axes orthogonal with respect to each other are illustrated as an X axis, a Y axis, and a Z axis.

Hereinafter, in the terahertz wave detecting device 200 according to the modification example of the present embodiment, members that have the same function as the constituent members of the terahertz wave detecting device 100 of the present embodiment will be designated by the same reference sign and will not be described in detail.

The terahertz wave detecting device 200 is different from the above terahertz wave detecting device 100 in that the plurality of unit cells 102 having different widths D of the second region 57 of the unit structure 55 is disposed.

The terahertz wave detecting device 200, as illustrated in FIG. 10, has four regions 200a, 200b, 200c, and 200d, and unit cells 102a, 102b, 102c, and 102d are respectively disposed in the regions 200a, 200b, 200c, and 200d. In the example illustrated, the planar shapes of the regions 200a, 200b, 200c, and 200d are squares. The regions 200a, 200b, 200c, and 200d, as illustrated in FIG. 10, may be divided by the layer 22 disposed on the substrate 10. Each of the unit cells 102a, 102b, 102c, and 102d is disposed in plural numbers in the regions 200a, 200b, 200c, and 200d.

The width D of the second region 57 of the unit structure 55 is different in each of the unit cells 102a, 102b, 102c, and 102d. That is, four types of unit cell 102 having different widths D of the second region 57 are disposed in the terahertz wave detecting device 200. The number of types of unit cell 102 is not limited to four.

The plurality of unit cells 102 having different widths D of the second region 57 of the unit structure 55 is disposed in the terahertz wave detecting device 200. Thus, the terahertz wave detecting device 200 can detect terahertz waves of different frequencies (different wavelengths).

The terahertz wave detecting device 200, like the terahertz wave detecting device 100, can have a high speed of reaction by decreasing a thermal capacity.

4. Imaging Apparatus

Figure 11:
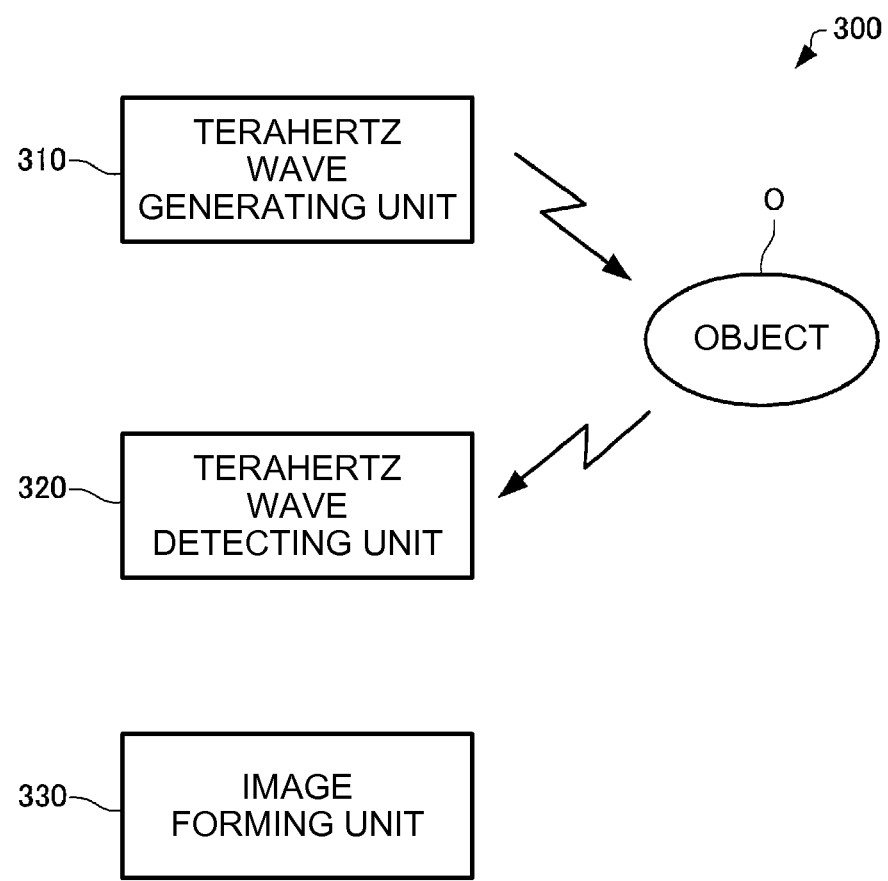
FIG. 11 is a block diagram schematically illustrating an imaging apparatus according to the embodiment.
Figure 12:
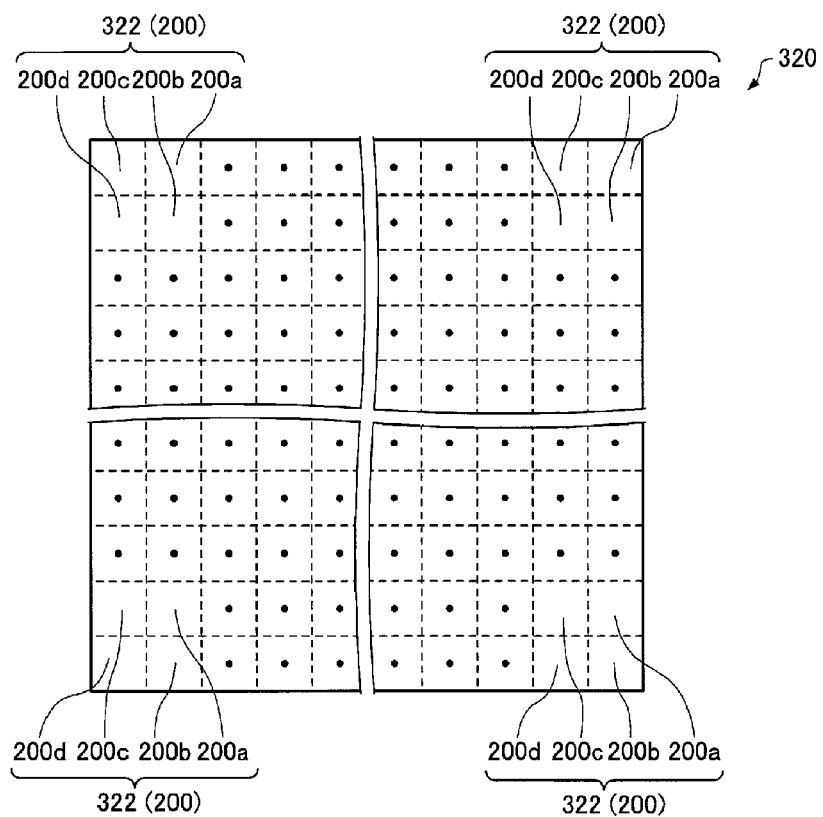
FIG. 12 is a plan view schematically illustrating a terahertz wave detecting unit of the imaging apparatus according to the embodiment.
Figure 13:
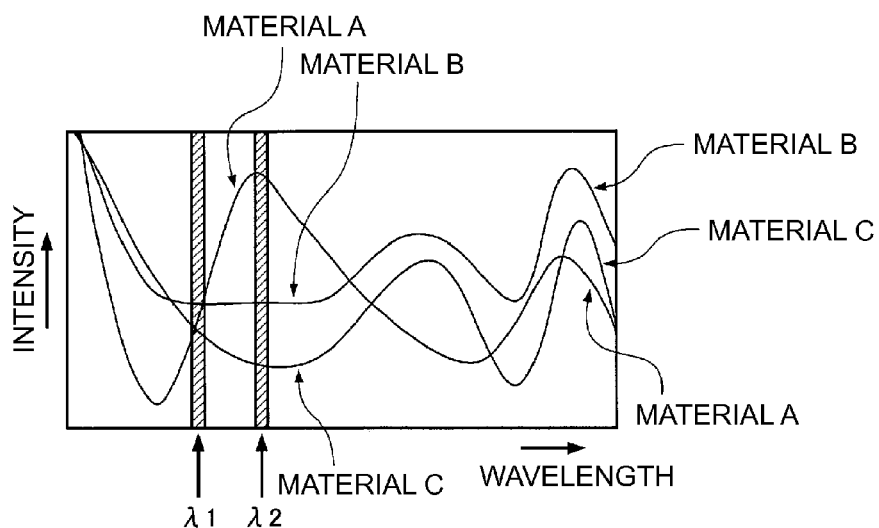
FIG. 13 is a graph illustrating the spectrum of an object in the terahertz band.
Figure 14:
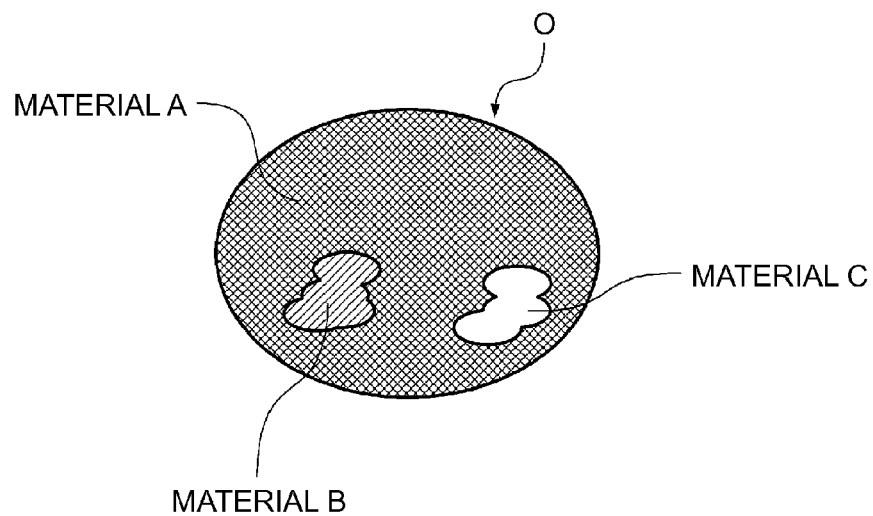
FIG. 14 is a diagram of an image illustrating a distribution of materials A, B, and C in the object.

Next, an imaging apparatus 300 according to the present embodiment will be described with reference to the drawings. FIG. 11 is a block diagram illustrating the imaging apparatus 300 according to the present embodiment. FIG. 12 is a plan view schematically illustrating a terahertz wave detecting unit 320 of the imaging apparatus 300 according to the present embodiment. FIG. 13 is a graph illustrating the spectrum of an object in the terahertz band. FIG. 14 is a diagram of an image illustrating a distribution of materials A, B, and C in the object.

The imaging apparatus 300, as illustrated in FIG. 11, includes a terahertz wave generating unit 310, the terahertz wave detecting unit 320, and an image forming unit 330. The terahertz wave generating unit 310 generates terahertz waves. The terahertz wave detecting unit 320 detects terahertz waves that are emitted from the terahertz wave generating unit 310 and that are transmitted through an object O or are reflected by the object O. The image forming unit 330 generates an image of the object O, that is, image data of the object O on the basis of a detection result of the terahertz wave detecting unit 320.

Types of terahertz wave generating unit 310 include, for example, a type that uses a quantum cascade laser, a photoconductive antenna, and a short pulse laser and a difference frequency generation type that uses a non-linear optic crystal.

The terahertz wave detecting unit 320 includes the terahertz wave detecting device according to the invention. Hereinafter, an example in which the terahertz wave detecting device 200 is included as the terahertz wave detecting device according to the invention will be described. In FIG. 12, the terahertz wave detecting device 200 is illustrated in a simplified manner for convenience of description.

The terahertz wave detecting unit 320 includes a plurality of pixels 322 as illustrated in FIG. 12. In the example illustrated, the shape of the pixels 322 is a square. The pixels 322 are arranged into a matrix. The number of pixels 322 is not particularly limited. The pixels 322 are configured of the terahertz wave detecting device 200.

In the terahertz wave detecting device 200, as described above, the unit cells 102a, 102b, 102c, and 102d that are respectively disposed in the regions 200a, 200b, 200c, and 200d can selectively detect terahertz waves of different wavelengths. That is, each of the pixels 322 can detect terahertz waves of four wavelengths.

Next, an example of the use of the imaging apparatus 300 will be described.

First, the object O that is the target of spectroscopic imaging is assumed to be configured of three materials A, B, and C. The imaging apparatus 300 performs spectroscopic imaging on the object O. As an example, the terahertz wave detecting unit 320 is assumed to detect terahertz waves that are reflected by the object O.

Each of the pixels 322 of the terahertz wave detecting unit 320 uses the unit cell 102a disposed in the region 200a and the unit cell 102b disposed in the region 200b of the terahertz wave detecting device 200. Given that $\lambda 1$, $\lambda 2$, $\alpha 1$, and $\alpha 2$ are respectively a wavelength detected (wavelength absorbed) in the unit cell 102a, a wavelength detected (wavelength absorbed) in the unit cell 102b, the intensity of components of terahertz waves in the wavelength $\lambda 1$ reflected by the object O, and the intensity of components of terahertz waves in the wavelength $\lambda 2$ reflected by the object O, the wavelength $\lambda 1$ detected in the unit cell 102a and the wavelength $\lambda 2$ detected in the unit cell 102b are set such that the difference $(\alpha 2-\alpha 1)$ between the intensity $\alpha 2$ and the intensity $\alpha 1$ can be significantly distinguished among the material A, the material B, and the material C.

For the material A, as illustrated in FIG. 13, the difference $(\alpha 2-\alpha 1)$ between the intensity $\alpha 2$ of components of terahertz waves in the wavelength $\lambda 2$ reflected by the object O and the intensity $\alpha 1$ of components of terahertz waves in the wavelength $\lambda 1$ reflected by the object O is a positive value. For the material B, the difference $(\alpha 2-\alpha 1)$ between the intensity $\alpha 2$ and the intensity $\alpha 1$ is zero. For the material C, the difference $(\alpha 2-\alpha 1)$ between the intensity $\alpha 2$ and the intensity $\alpha 1$ is a negative value.

When the imaging apparatus 300 performs spectroscopic imaging on the object O, first, the terahertz wave generating unit 310 generates terahertz waves, and the object O is irradiated with the terahertz waves. Then, the terahertz wave detecting unit 320 detects terahertz waves reflected by the object O as $\alpha 1$ and $\alpha 2$. This detection result is transmitted to the image forming unit 330. The irradiation of the object O with terahertz waves and the detection of terahertz waves reflected by the object O are performed on the entire object O.

The image forming unit 330, on the basis of the detection result, obtains the difference $(\alpha 2-\alpha 1)$ between the intensity $\alpha 2$ of components of terahertz waves in the wavelength $\lambda 2$ detected in the unit cell 102b and the intensity $\alpha 1$ of components of terahertz waves in the wavelength $\lambda 1$ detected in the unit cell 102a. Then, the part of the object O where the difference is a positive value is determined and specified as the material A, the part of the object O where the difference is zero as the material B, and the part of the object O where the difference is a negative value as the material C.

The image forming unit 330, as illustrated in FIG. 14, creates image data of an image that illustrates a distribution of the materials A, B, and C in the object O. This image data is transmitted to an unillustrated monitor from the image forming unit 330, and the image that illustrates a distribution of the materials A, B, and C in the object O is displayed on the monitor. In this case, regions of the object O where each material is distributed are differentiated in color. For example, the region of the material A is displayed in black, the region of the material B in gray, and the region of the material C in white. In the imaging apparatus 300, as described herebefore, identification of each material constituting the object O and measurement of a distribution of each material can be performed simultaneously. The imaging apparatus 300 is used in, for example, testing medicines.

The application of the imaging apparatus 300 is not limited to the above example. For example, the imaging apparatus 300 can be used in determining whether a person carries a pistol, a knife, an illegal drug, and the like by irradiating the person with terahertz waves, detecting terahertz waves that are transmitted through or reflected by the person, and performing processes in the image forming unit 330.

The imaging apparatus 300 includes the terahertz wave detecting device 200 that can have a high speed of reaction by decreasing a thermal capacity. Thus, the imaging apparatus 300 can have a high speed of reaction.

5. Measuring Apparatus

Figure 15:
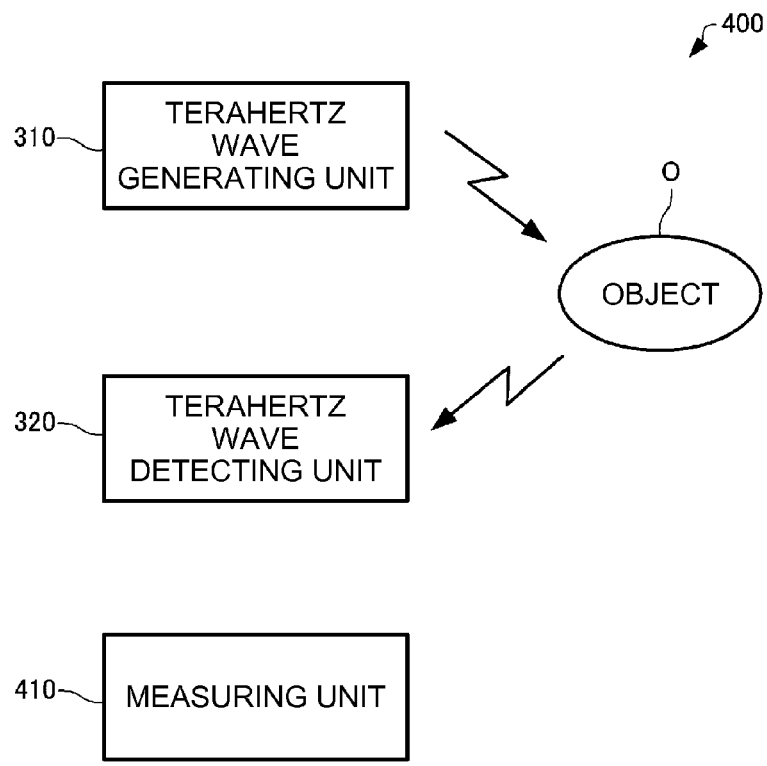
FIG. 15 is a block diagram schematically illustrating a measuring apparatus according to the embodiment.

Next, a measuring apparatus 400 according to the present embodiment will be described with reference to the drawings. FIG. 15 is a block diagram illustrating the measuring apparatus 400 according to the present embodiment.

Hereinafter, in the measuring apparatus 400 according to the present embodiment, members that have the same function as the constituent members of the imaging apparatus 300 of the present embodiment will be designated by the same reference sign and will not be described in detail. This also applies to a below-described camera 500 of the present embodiment.

The measuring apparatus 400, as illustrated in FIG. 15, includes the terahertz wave generating unit 310, which generates terahertz waves, the terahertz wave detecting unit 320, which detects terahertz waves emitted from the terahertz wave generating unit 310 and transmitted through or reflected by the object O, and a measuring unit 410. The measuring unit 410 measures the object O on the basis of the detection result of the terahertz wave detecting unit 320.

Next, an example of the use of the measuring apparatus 400 will be described. When the measuring apparatus 400 performs spectroscopic measurement on the object O, first, the terahertz wave generating unit 310 generates terahertz waves, and the object O is irradiated with the terahertz waves. Then, the terahertz wave detecting unit 320 detects terahertz waves that are transmitted through the object O or terahertz waves that are reflected by the object O. This detection result is transmitted to the measuring unit 410. The irradiation of the object O with terahertz waves and the detection of terahertz waves transmitted through the object O or reflected by the object O are performed on the entire object O.

In the measuring unit 410, each intensity of terahertz waves detected in the unit cells 102a, 102b, 102c, and 102d of the terahertz wave detecting device 200 that constitutes each of the pixels 322 is obtained from the detection result, and an analysis and the like of the components and the distribution of the object O are performed.

The measuring apparatus 400 includes the terahertz wave detecting device 200 that can have a high speed of reaction by decreasing a thermal capacity. Thus, the measuring apparatus 400 can have a high speed of reaction.

6. Camera

Figure 16:
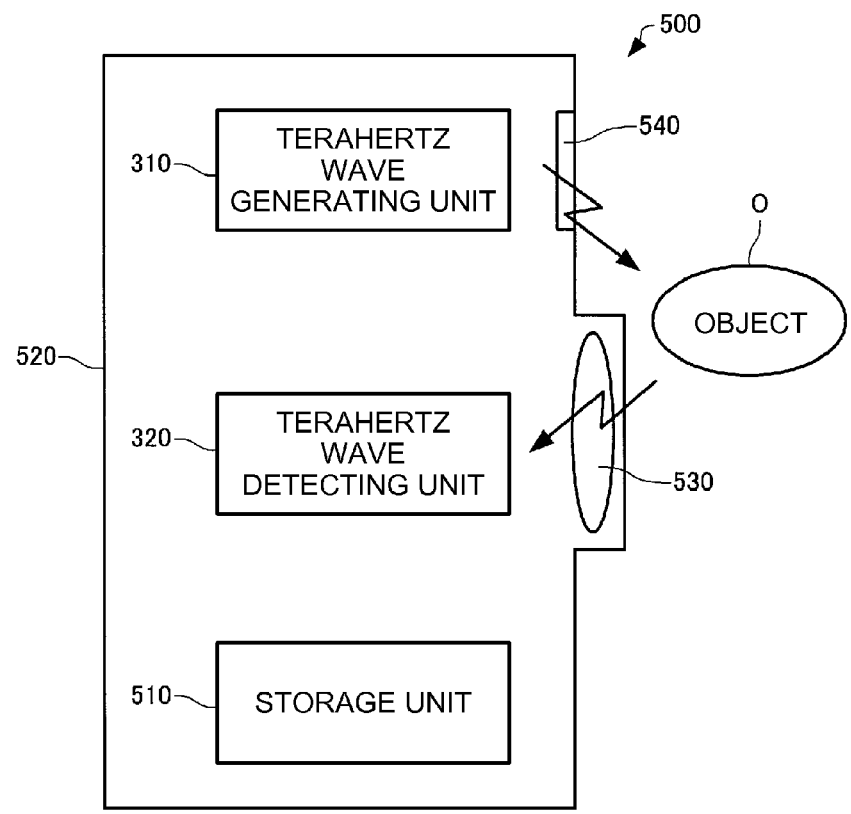
FIG. 16 is a block diagram schematically illustrating a camera according to the embodiment.
Figure 17:
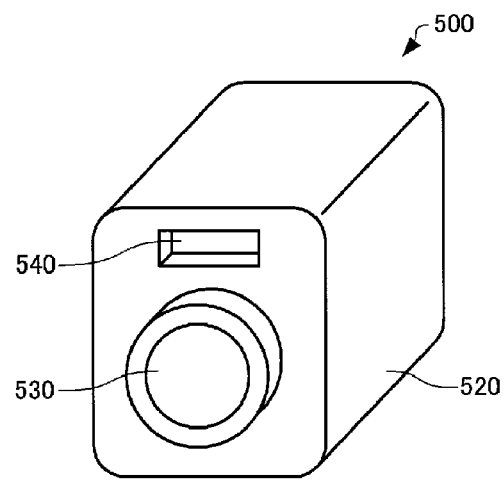
FIG. 17 is a perspective view schematically illustrating the camera according to the embodiment.

Next, the camera 500 according to the present embodiment will be described with reference to the drawings. FIG. 16 is a block diagram illustrating the camera 500 according to the present embodiment. FIG. 17 is a perspective view schematically illustrating the camera 500 according to the present embodiment.

The camera 500, as illustrated in FIG. 16 and FIG. 17, includes the terahertz wave generating unit 310, which generates terahertz waves, the terahertz wave detecting unit 320, which detects terahertz waves emitted from the terahertz wave generating unit 310 and transmitted through or reflected by the object O, and a storage unit 510. The storage unit 510 stores the detection result of the terahertz wave detecting unit 320. Each of these units 310, 320, and 510 are accommodated in a casing 520 of the camera 500. The camera 500 is also provided with a lens (optical system) 530 and a window portion 540. The lens 530 causes terahertz waves reflected by the object O to converge (to be imaged) toward the terahertz wave detecting unit 320. The window portion 540 is used for emitting terahertz waves generated by the terahertz wave generating unit 310 outside of the casing 520. The lens 530 and the window portion 540 are configured of a member that transmits or refracts terahertz waves, such as silicon, quartz, and polyethylene. The window portion 540 may be configured to be simply disposed as an opening such as a slit.

Next, an example of the use of the camera 500 will be described. When the camera 500 captures an image of the object O, first, the terahertz wave generating unit 310 generates terahertz waves, and the object O is irradiated with the terahertz waves. Then, the lens 530 causes terahertz waves reflected by the object O to converge (to be imaged) toward the terahertz wave detecting unit 320 and to be detected. This detection result is transmitted to the storage unit 510 and is stored thereon. The irradiation of the object O with terahertz waves and the detection of terahertz waves reflected by the object O are performed on the entire object O. The detection result can be transmitted to an external device such as a personal computer. The personal computer can perform various processes on the basis of the detection result.

The camera 500 includes the terahertz wave detecting device 200 that can have a high speed of reaction by decreasing a thermal capacity. Thus, the camera 500 can have a high speed of reaction.

The above embodiment and modification example are for illustrative purposes only, and the invention is not limited thereto. For example, an appropriate combination of the embodiment and the modification example may also be provided.

The invention includes a configuration which is substantially the same as the configuration described in the embodiment (for example, a configuration having the same function, method, and result or a configuration having the same object and effect). The invention also includes a configuration in which a non-essential part of the configuration described in the embodiment is substituted. The invention also includes a configuration capable of accomplishing the same effect or achieving the same object as the configuration described in the embodiment. The invention also includes a configuration that results from adding a known technology to the configuration described in the embodiment.

The entire disclosure of Japanese Patent Application No. 2014-194032, filed Sep. 24, 2014 is expressly incorporated by reference herein.

What is claimed is:

1. A terahertz wave detecting device comprising:
a substrate;
a first metal layer that is disposed above the substrate;
a pyroelectric layer that is disposed on the first metal layer; and
a second metal layer that is disposed on the pyroelectric layer,
wherein the second metal layer has a periodic structure in which a unit structure is disposed in a predetermined period, and
wherein the pyroelectric layer absorbs terahertz waves being incident on the pyroelectric layer and converts the terahertz waves into heat and converts the converted heat into an electrical signal, wherein the first metal layer, the pyroelectric layer, and the second metal layer constitute a unit cell,
wherein the unit cell is disposed in plural numbers,
wherein the unit structure includes:
  a region on the pyroelectric layer where the second metal layer is disposed, and
  a region on the pyroelectric layer where the second metal layer is not disposed, and
wherein the unit cell is disposed in plural numbers having different widths of the region where the second metal layer is not disposed.

2. The terahertz wave detecting device according to claim 1,
wherein the predetermined period is shorter than the wavelength of the terahertz waves in a vacuum that are absorbed into the pyroelectric layer.

3. The terahertz wave detecting device according to claim 1,
wherein the first metal layer and the second metal layer are electrically connected to the pyroelectric layer.

4. The terahertz wave detecting device according to claim 1, further comprising:
a supportive substrate that supports the first metal layer; and
a supportive portion that supports the supportive substrate separately from the substrate.

5. The terahertz wave detecting device according to claim 1,
wherein the thickness of the pyroelectric layer is greater than or equal to 300 nm and less than or equal to 700 nm.

6. The terahertz wave detecting device according to claim 1, further comprising:
a reflective layer that reflects the terahertz waves below the first metal layer.

7. A camera comprising:
a terahertz wave generating unit that generates terahertz waves;
a terahertz wave detecting unit that includes the terahertz wave detecting device according to claim 1 which detects the terahertz waves emitted from the terahertz wave generating unit and transmitted through or reflected by an object; and
a storage unit that stores a detection result of the terahertz wave detecting unit.

8. An imaging apparatus comprising:
a terahertz wave generating unit that generates terahertz waves;
a terahertz wave detecting unit that includes the terahertz wave detecting device according to claim 1 which detects the terahertz waves emitted from the terahertz wave generating unit and transmitted through or reflected by an object; and
an image forming unit that generates an image of the object on the basis of a detection result of the terahertz wave detecting unit.

9. A measuring apparatus comprising:
a terahertz wave generating unit that generates terahertz waves;
a terahertz wave detecting unit that includes the terahertz wave detecting device according to claim 1 which detects the terahertz waves emitted from the terahertz wave generating unit and transmitted through or reflected by an object; and
a measuring unit that measures the object on the basis of a detection result of the terahertz wave detecting unit.

10. A camera comprising:
a terahertz wave generating unit that generates terahertz waves;
a terahertz wave detecting unit that includes the terahertz wave detecting device according to claim 2 which detects the terahertz waves emitted from the terahertz wave generating unit and transmitted through or reflected by an object; and
a storage unit that stores a detection result of the terahertz wave detecting unit.

11. An imaging apparatus comprising:
a terahertz wave generating unit that generates terahertz waves;
a terahertz wave detecting unit that includes the terahertz wave detecting device according to claim 2 which detects the terahertz waves emitted from the terahertz wave generating unit and transmitted through or reflected by an object; and
an image forming unit that generates an image of the object on the basis of a detection result of the terahertz wave detecting unit.

12. A measuring apparatus comprising:
a terahertz wave generating unit that generates terahertz waves;
a terahertz wave detecting unit that includes the terahertz wave detecting device according to claim 2 which detects the terahertz waves emitted from the terahertz wave generating unit and transmitted through or reflected by an object; and
a measuring unit that measures the object on the basis of a detection result of the terahertz wave detecting unit.

13. A camera comprising:
a terahertz wave generating unit that generates terahertz waves;
a terahertz wave detecting unit that includes the terahertz wave detecting device according to claim 3 which detects the terahertz waves emitted from the terahertz wave generating unit and transmitted through or reflected by an object; and
a storage unit that stores a detection result of the terahertz wave detecting unit.

14. An imaging apparatus comprising:
a terahertz wave generating unit that generates terahertz waves;
a terahertz wave detecting unit that includes the terahertz wave detecting device according to claim 3 which detects the terahertz waves emitted from the terahertz wave generating unit and transmitted through or reflected by an object; and
an image forming unit that generates an image of the object on the basis of a detection result of the terahertz wave detecting unit.

15. A measuring apparatus comprising:
a terahertz wave generating unit that generates terahertz waves;
a terahertz wave detecting unit that includes the terahertz wave detecting device according to claim 3 which detects the terahertz waves emitted from the terahertz wave generating unit and transmitted through or reflected by an object; and
a measuring unit that measures the object on the basis of a detection result of the terahertz wave detecting unit.

16. A camera comprising:
a terahertz wave generating unit that generates terahertz waves;
a terahertz wave detecting unit that includes the terahertz wave detecting device according to claim 4 which detects the terahertz waves emitted from the terahertz wave generating unit and transmitted through or reflected by an object; and a storage unit that stores a detection result of the terahertz wave detecting unit.

17. An imaging apparatus comprising:

a terahertz wave generating unit that generates terahertz waves;

a terahertz wave detecting unit that includes the terahertz wave detecting device according to claim 4 which detects the terahertz waves emitted from the terahertz wave generating unit and transmitted through or reflected by an object; and an image forming unit that generates an image of the object on the basis of a detection result of the terahertz wave detecting unit.

18. A measuring apparatus comprising:

a terahertz wave generating unit that generates terahertz waves;

a terahertz wave detecting unit that includes the terahertz wave detecting device according to claim 4 which detects the terahertz waves emitted from the terahertz wave generating unit and transmitted through or reflected by an object; and a measuring unit that measures the object on the basis of a detection result of the terahertz wave detecting unit.

* * * * *